United States Patent [19]

Daley et al.

[11] 3,960,782

[45] June 1, 1976

[54] SHAMPOO COMPOSITIONS WHICH IMPART HIGH LUSTER AND MANAGEABILITY TO HAIR

[75] Inventors: Edwin W. Daley, Cincinnati; M. Pauline Yowler, Springfield Township, Hamilton County, both of Ohio

[73] Assignee: The Procter & Gamble Company, Cincinnati, Ohio

[22] Filed: Sept. 27, 1974

[21] Appl. No.: 509,995

[52] U.S. Cl. ............................... 252/544; 252/153; 252/DIG. 13
[51] Int. Cl.$^2$ ...................... C11D 1/30; C11D 3/26
[58] Field of Search ............ 252/544, DIG. 13, 153, 252/548; 424/70; 8/10.2

[56] References Cited
UNITED STATES PATENTS

| | | | |
|---|---|---|---|
| 2,374,187 | 4/1945 | Flett | 252/544 |
| 2,535,972 | 12/1950 | Vitalis | 252/544 |
| 2,674,580 | 4/1954 | Henkin | 252/DIG. 13 |
| 2,675,356 | 4/1954 | Woodworth et al. | 252/110 |
| 2,773,835 | 12/1956 | Anderson | 252/153 |
| 2,871,193 | 1/1959 | Henkin | 252/548 X |
| 3,149,042 | 9/1964 | Habicht et al. | 424/70 |
| 3,723,325 | 3/1973 | Parron | 252/DIG. 13 |

FOREIGN PATENTS OR APPLICATIONS

| | | | |
|---|---|---|---|
| 781,384 | 9/1972 | Belgium | 8/10.2 |

OTHER PUBLICATIONS

Sagarin, Edward, Cosmetics Science and Technology, 1st Ed., p. 405, 1957, Interscience Publishers, Inc., New York.

*Primary Examiner*—Thomas J. Herbert, Jr.
*Attorney, Agent, or Firm*—Ronald L. Hemingway; George W. Allen; Richard C. Witte

[57] ABSTRACT

Shampoo compositions which impart luster and manageability to the hair, said compositions comprising an alkyl sulfate or alkyl monoglyceride sulfonate surfactant, urea, dodecyl alcohol and guanidine or a water-soluble salt thereof, said compositions having a pH of from about 5 to about 8.

6 Claims, No Drawings

SHAMPOO COMPOSITIONS WHICH IMPART HIGH LUSTER AND MANAGEABILITY TO HAIR

BACKGROUND OF THE INVENTION

1. Field of the Invention

This invention relates to shampoos which impart both luster and manageability to the hair. These shampoos also have excellent foaming and cleaning properties and impart longer-lasting cleanliness to the hair.

2. Description of the Prior Art

All of the individual components of the compositions of the present invention have been used previously in compositions for treating the hair; however, the unique combination of these ingredients to produce the outstanding luster and manageability characteristics which are achieved with the present invention has not been previously described. U.S. Pat. No. 3,723,325, Parran, issued Mar. 27, 1973, discloses the use of alkyl sulfate and monoglyceride sulfonate surfactants in shampoos. Sagarin, *Cosmetics Science and Technology*, 1st Ed. (1957) at page 405 discloses urea as a suitable conditioning agent for shampoos because of its moisture-retaining properties. Guanidine salts as components of hair dyeing compositions are disclosed in Belgian Pat. No. 781,384, granted Sept. 29, 1972. U.S. Pat. No. 2,871,193, Henkin, issued Jan. 27, 1959, discloses shampoos containing monoglyceride sulfate surfactants, with fatty alcohols and urea as optional additional components.

DESCRIPTION OF THE INVENTION

The present invention relates to shampoo compositions which have excellent foaming and cleaning properties and which additionally impart to the hair excellent manageability, a high luster and excellent cleanliness retention. It has been found that the shampoos herein tend to roughen the surface of the hair and this is believed to be the reason why they make the hair more manageable than conventional shampoos. Surprisingly, however, notwithstanding this roughening of the hair, which would be expected to detract from luster, the shampoos herein impart an exceptionally high degree of luster to the hair. Use of the shampoo compositions herein also appears to inhibit the flow of sebum up the hair shaft of the washed hair, thereby resulting in longer-lasting cleanliness to the hair and corresponding reduction in the necessary frequency of shampooing the hair.

The shampoos of the present invention comprise:

A. from about 8 to about 22 percent of a surfactant which is the water-soluble salt of an alkyl sulfate or a fatty acid monoglyceride sulfonate;
B. from about 2 to about 15 percent urea;
C. from about 1 to about 10 percent of a water-soluble quanidine salt; and
D. from about 0.2 to about 2.0 percent dodecyl alcohol.

All percentages herein are by weight unless otherwise specified.

It is believed that the unique combination of properties obtained with the compositions herein are the result of an interaction among the alkyl sulfate or monoglyceride sulfonate surfactant, urea, guanidine and dodecanol since elimination of one of these ingredients, or substitution of various other surfactants for the alkyl sulfate or monoglyceride sulfonate results in a dramatic reduction in one or more of these desirable properties.

The monoglyceride sulfonate surfactants used in the present compositions are well known in the art and have the general formula:

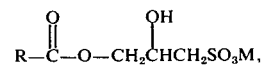

wherein R is an alkyl group and M is a salt-forming cation. They can be prepared, for example, by reacting epichlorohydrin with sodium bisulfite to produce 2,3-epoxy-1-propane sulfonic acid, which is neutralized with sodium hydroxide to form sodium 2,3-dihydroxy-1-propane sulfonate. This, in turn, is reacted with a fatty acid in a conventional esterification reaction to produce fatty acid monoglyceride sodium sulfonate. Any water-soluble salt of fatty acid monoglyceride sulfonate (e.g., those having a solubility of greater than 0.01% by weight in water at 25°C.) can be used in the present compositions. Examples of such salts are the alkali metal (e.g., sodium and potassium) ammonium and low molecular weight substituted ammonium salts. Examples of these latter salts are the mono-, di- and tri-$C_1$ to $C_3$ alkyl and alkanolamine salts, e.g., diethylamine, triisopropylamine, monoethanol-, diethanol- and triethanolamine salts. The fatty acid moiety of the monoglyceride sulfonate surfactant can range in chain length from about $C_8$ to about $C_{22}$, preferably from about $C_8$ to about $C_{18}$, and most preferably is about $C_{12}$. The fatty acid moiety can be of natural or synthetic origin. Coconut fatty acids, which have an average chain length of about $C_{12}$, are particularly suitable for preparing the monoglyceride sulfonate surfactants herein. Likewise, the alkyl sulfate surfactants herein are well known surfactants, having the formula RO-$SO_3M$, wherein R is an alkyl group and M is a salt-forming cation. The R can be derived from natural or synthetic fatty alcohols having a chain length of from about 8 to 22, preferaby 8 to 18, and most preferably about 12 carbon atoms. Coconut fatty alcohol which has an average chain length of about 12 carbon atoms is particularly suitable for preparing the alkyl sulfates herein. The M is any salt-forming cation suitable for rendering the alkyl sulfate soluble in water to the extent of at least 0.01 at 25°C. The salts exemplified above for fatty acid monoglyceride sulfonates are also suitable for alkyl sulfates. The amount of alkyl sulfate or fatty acid monoglyceride sulfonate surfactant in the compositions is from about 8 to about 22 percent, preferably from about 12 to about 20 percent. The fatty acid monoglyceride sulfonate and alkyl sulfate surfactants can be used in combination in the compositions herein.

The amount of urea in the compositions herein ranges from about 2 to about 15 percent, and is preferably from about 3 to 8 percent.

The guanidine or its water-soluble salts are present in the compositions herein at a level of from about 1 to about 10 percent, preferably from about 2 to about 6 percent. Any water-soluble guanidine salt (e.g., having a solubility of greater than 0.01 percent in water at 25°C.) can be used. Such salts are formed by reacting guanidine with an acid, e.g., mineral acids such as hydrochloric and hydrobromic acid, oxyacids such as phosphoric, sulfuric, carbonic and nitric, and organic acids such as formic, acetic, chloroacetic and the like. Guanidine hydrochloride is a preferred salt.

The dodecanol used in the shampoos herein can be of either natural or synthetic origin and comprises from about 0.2 to 2.0 percent, preferably from about 0.5 to about 1.5 percent, of the composition. Although higher and lower homologs of dodecanol can also be present, the use of pure dodecanol is preferred.

The pH of the shampoo compositions herein should lie in the range of 5.0 to 8.0, preferably 6.0 to 7.0. pH can be adjusted to the desired level by using conventional pH adjusting agents such as those described hereinbelow.

The shampoos herein are preferably in the form of liquids or creams in which water is the principal diluent. The level of water in the compositions is typically from about 40% to about 85%. Other ingredients which are conventional in the formulation of shampoos can also be present, e.g., preservatives such as benzyl alcohol, thickeners and viscosity modifiers such as sodium chloride, sodium sulfate, carboxymethylcellulose, polyvinyl alcohol, and ethyl alcohol, pH adjusting agents such as citric acid, phosphoric acid, sodium hydroxide, sodium carbonate, etc., perfumes, dyes, opacifiers such as behenic acid and calcium stearate, antidandruff agents such as sulfur and zinc pyridinethiol-N-oxide, and sequestering agents such as disodium ethylenediaminetetraacetate.

The following examples will illustrate the invention but are not intended to be in any way limiting thereof.

EXAMPLE I

A shampoo composition is prepared by mixing the following ingredients.

| Component | Parts by Weight |
|---|---|
| Coconut fatty acid monoglyceride sodium sulfonate | 16.00 |
| Urea | 5.00 |
| Guanidine hydrochloride | 2.50 |
| Dodecyl alcohol | 0.90 |
| Benzyl alcohol | 1.00 |
| Sodium chloride | 0.10 |
| Perfume | 0.25 |
| Water | 74.25 |
| | 100.00 |
| pH 6.4 | |

Use of this shampoo in the conventional manner results in the imparting of excellent luster and manageability to the hair. It is also noted that the hair tends to remain clean for a longer period of time compared to hair which has been shampooed with conventional shampoos.

EXAMPLE II

A shampoo composition is prepared by mixing the following ingredients.

| Component | Parts by Weight |
|---|---|
| Coconut fatty acid monoglyceride sodium sulfonate | 16.00 |
| Sodium coconut alkyl sulfate | 1.10 |
| Urea | 5.00 |
| Guanidine hydrochloride | 2.50 |
| Dodecyl alcohol | 0.70 |
| Water | 74.70 |
| | 100.00 |
| pH 6.0 | |

Use of this shampoo in the conventional manner results in the imparting of excellent luster and manageability to the hair. It is also noted that the hair tends to remain clean for a longer period of time compared to hair which has been shampooed with conventional shampoos.

EXAMPLE III

A shampoo composition is prepared by mixing the following ingredients.

| Component | Parts by Weight |
|---|---|
| Coconut fatty acid monoglyceride sodium sulfonate | 16.00 |
| Sodium coconut alkyl sulfate | 1.10 |
| Urea | 10.00 |
| Guanidine hydrochloride | 5.00 |
| Dodecyl alcohol | 1.40 |
| Water | 66.50 |
| | 100.00 |
| pH 6.8 | |

Use of this shampoo in the conventional manner results in the imparting of excellent luster and manageability to the hair. It is also noted that the hair tends to remain clean for a longer period of time compared to hair which has been shampooed with conventional shampoos.

EXAMPLE IV

A shampoo composition is prepared by mixing the following ingredients.

| Component | Parts by Weight |
|---|---|
| Coconut fatty acid monoglyceride sodium sulfonate | 19.70 |
| Sodium coconut alkyl sulfate | 1.40 |
| Urea | 5.60 |
| Guanidine hydrochloride | 2.80 |
| Dodecyl alcohol | 0.90 |
| Water | 69.60 |
| | 100.00 |
| pH 6.8 | |

Use of this shampoo in the conventional manner results in the imparting of excellent luster and manageability to the hair. It is also noted that the hair tends to remain clean for a longer period of time compared to hair which has been shampooed with conventional shampoos.

EXAMPLE V

A shampoo composition is prepared by mixing the following ingredients.

| Component | Parts by Weight |
|---|---|
| Triethanolamine alkyl sulfate | 17.50 |
| Coconut ethanolamide | 5.00 |
| Guanidine hydrochloride | 2.50 |
| Urea | 5.00 |
| Dodecyl alcohol | 0.90 |
| Methocel 60 HG | 0.65 |
| Perfume | 0.25 |

| Component | Parts by Weight |
|---|---|
| Na₄ EDTA | 0.14 |
| Ethanol, SDA No. 40 | 7.00 |
| Water | 61.06 |
| | 100.00 |
| pH 7.0 | |

Use of this shampoo in the conventional manner results in the imparting of excellent luster and manageability to the hair. It is also noted that the hair tends to remain clean for a longer period of time compared to hair which has been shampooed with conventional shampoos.

What is claimed is:

1. A shampoo composition comprising:
  A. from about 8 to about 22 percent of a surfactant selected from the group consisting of
   1. water-soluble salts of a fatty acid monoglyceride sulfonate of the formula

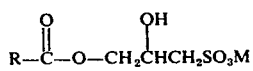

wherein

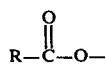

is a fatty acid moiety containing from about 8 to 22 carbon atoms and wherein M is a salt-forming cation; and
   2. water-soluble salts of an alkyl sulfate wherein the alkyl group contains from about 8 to about 22 carbon atoms;
  B. from about 2 to about 15 percent urea;
  C. from about 1 to about 10 percent of guanidine or a water-soluble salt thereof; and
  D. from about 0.2 to about 2.o percent of dodecyl alcohol;

said composition having a pH of from about 5 to about 8.

2. The composition of claim 1 wherein the amount of component (A) is from about 12 to about 20 percent, the amount of component (B) is from about 3 to about 8 percent, the amount of component (C) is from about 2 to about 6 percent, and the amount of component (D) is from about 0.5 to about 1.5 percent.

3. The composition of claim 2 wherein the fatty acid moiety of component (A)(1) contains from about 8 to about 18 carbon atoms and the alkyl group in component (A)(2) contains from 8 to about 18 carbon atoms.

4. The composition of claim 3 wherein the fatty acid moiety of component (A)(1) is coconut fatty acid and the alkyl moiety in component (A)(2) is coconut alkyl.

5. The composition of claim 3 wherein component (D) is guanidine hydrochloride.

6. The composition of claim 3 wherein the pH is from about 6 to about 7.

* * * * *